United States Patent [19]
Cunningham et al.

[11] Patent Number: 5,753,243
[45] Date of Patent: May 19, 1998

[54] PLASTICIZED HIGH WATER CONTENT COSMETIC GEL COMPOSITION AND PENCIL THEREFORE

[75] Inventors: John Cunningham, Franklin; Angie W. Sanders; Wista M. Crawford, both of Lewisburg, all of Tenn.

[73] Assignee: Cosmolab, Inc., Lewisburg, Tenn.

[21] Appl. No.: 742,207

[22] Filed: Oct. 31, 1996

[51] Int. Cl.$^6$ ............................................. A61K 7/00
[52] U.S. Cl. ........................ 424/401; 424/59; 424/65; 132/318
[58] Field of Search .................... 424/401, 59, 65, 424/64; 132/318

[56] References Cited

U.S. PATENT DOCUMENTS

| | | | |
|---|---|---|---|
| 4,226,889 | 10/1980 | Yuhas | 424/59 |
| 4,322,400 | 3/1982 | Yuhas | 424/59 |
| 4,923,478 | 5/1990 | Naggiar | 8/161 |
| 5,114,711 | 5/1992 | Kuznitz et al. | 424/401 |
| 5,128,123 | 7/1992 | Brewster et al. | 424/65 |
| 5,258,136 | 11/1993 | Smith et al. | 252/315.4 |
| 5,424,070 | 6/1995 | Kasat et al. | 424/401 |
| 5,443,821 | 8/1995 | Smith et al. | 424/65 |
| 5,462,736 | 10/1995 | Rech et al. | 424/401 |
| 5,585,092 | 12/1996 | Trandai | 424/65 |

FOREIGN PATENT DOCUMENTS

WO91/04383  5/1990  WIPO.

*Primary Examiner*—Imurman K. Page
*Assistant Examiner*—D. Faulkner
*Attorney, Agent, or Firm*—Fitzpatrick, Cella, Harper & Scinto

[57] ABSTRACT

A plasticized high water content cosmetic gel that will be sharpenable when used as a core inside of a sharpenable pencil barrel. The gel essentially comprises, by weight, about 25–42% water; about 25–35% of a polyol or aliphatic diol vehicle such as a butylene glycol; about 4–12% sodium stearate; about 0.1–2% of a carboxylated acid ester plasticizer; about 4–28% of a colorant; and about 0.1–1% of a surfactant. To reduce syneresis, adding about 1 percent or less a viscosity increasing agent is effective. For water resistance when the cosmetic gel is applied to a user's skin, adding about 5–10% of a styrene acrylic polymer waterproofing agent is effective, and does not increase irritation levels out of the mild range.

28 Claims, No Drawings

PLASTICIZED HIGH WATER CONTENT COSMETIC GEL COMPOSITION AND PENCIL THEREFORE

BACKGROUND OF THE INVENTION

1. Field of the Invention

The invention relates generally to cosmetic gel compositions, and in particular relates to a plasticized, high water content cosmetic gel composition in a sharpenable pencil configuration.

2. Brief Description of the Related Art

In the cosmetics field, it is well-known that high water content cosmetic sticks (cosmetic sticks with water contents of about 10 percent to about 50 percent) are useful for certain applications, such as gel deodorants. Generally, if a gel composition is firm enough to support its own mass, the water content is too low to be effective (i.e. about 2 percent to about 5 percent). On the other hand, if the composition contains enough water to be effective (i.e. about 10 percent to about 50 percent), the composition is usually too soft to be able to support itself.

Examples of common formulations for sodium stearate gels used primarily for deodorants are illustrated by the U.S. patents, which are incorporated herein by reference for that purpose, as follows:

U.S. Pat. No. 5,462,736 CRYSTAL CLEAR COSMETIC STICK COMPOSITION

U.S. Pat. No. 5,443,821 ALKOXYLATED COMPOUNDS AND USE IN COSMETIC STICK

U.S. Pat. No. 5,424,070 TRANSPARENT CLEAR STICK COMPOSITION

These patents do not address any modifications of those gel characteristics which are important to the present invention. For example, none address addition of colorants, or a gel designed to be sharpened as a pencil core. The gels illustrated therein are not designed for applying color to the skin, and would be applied to the axilla, not the face or eyes of an end user.

Consequently, high water content cosmetic compositions must be contained in various forms of packaging. Known forms of packaging require special seals to retain the effusive nature of the water in the compositions. If the water is allowed to evaporate, the compositions would become unsightly and non-functional.

In response to the above requirements, it has become common practice either to insert, or mold directly, a high water content cosmetic as a stick into a plastic housing. Soft cosmetics such as blusher, or gel deodorant, in plastic, push-up dispenser-type containers are quite familiar to consumers. For example, since 1960 deodorant gel sticks comprising sodium stearate, alcohol, water and propylene glycol have been in common use. The blunt face of such a stick typically is used to apply a wide swath, about 1 inch wide, of deodorant or antiperspirant gel to the skin. Blusher gel sticks are another well-known type of non-sharpenable cosmetic sticks.

Until the present invention, high water content cosmetic compositions have not been usable as a core in a sharpenable pencil barrel housing. Instead, anhydrous wax or oil cosmetic compositions have been used as cores of pencil barrels, because the sharpenability of anhydrous compositions is easily improved by a plasticization. Unlike anhydrous compositions, known high water content cosmetic compositions are difficult to plasticize. A plasticizer ideally permits more pressure to be applied to a point without suffering breakage. If too brittle, a core will break off during application. If too soft, a core will crumble in use or not be sharpenable in the first place.

If any high water content cosmetic gel composition is to find utility as the core composition inside a pencil barrel housing, the composition must be plasticized to that degree which will create the strength and flexibility necessary for smooth sharpening. Lip liners and eye liners must be sharpenable. Cosmetic compositions that have not been plasticized would crumble or break off during sharpening. Furthermore, unplasticized or overly brittle compositions would break off during use and therefore provide poor application to the skin.

Heretofore, no attempts have been made to provide a plasticized (in other words, sharpenable) high water content cosmetic gel composition for use in a pencil barrel housing. This primarily was due to the fact that the water cannot be contained in typical barrel compositions, i.e., wood, styrene or polyethylene and also because known high water content compositions were thought to be too irritating to the skin.

SUMMARY OF THE INVENTION

A first object of the present invention is to provide a plasticized high water content cosmetic gel composition which can be sharpened and used as a cosmetic alone or as the core composition inside of a pencil barrel housing.

A second object of the present invention is to provide a cosmetic gel composition of high water content, which can be sharpened and which also will payout a cosmetic that will be relatively water resistant, on the skin.

A third object of the present invention is to provide a sharpenable apparatus for gel cosmetic storage and application (hereafter referred to as a "gel pencil"). The gel pencil essentially comprises the sharpenable combination of pencil barrel housing surrounding a core of a plasticized high water content cosmetic gel composition.

A plasticized high water content cosmetic gel composition according to the first object of the present invention essentially may be defined using the following components in the indicated useful percentage ranges, by weight (with preferences shown in parentheses), as follows:

| Component | Low | Preferred | High |
| --- | --- | --- | --- |
| Water | 25 | 33 | 42 |
| Aliphatic Diol | 25 | 29 | 35 |
| Sodium Stearate | 4 | 8 | 12 |
| Plasticizer (Velsan P8-3) | 0.1 | 0.25 | 2 |
| Colorants | 4 | 16 | 28 |
| Surfactant (Procetyl AWS) | 0.1 | 0.2 | 1 |

The plasticized high water content cosmetic gel composition further may include about 10% glycerin, a viscosity increasing agent (or thickener) and optionally certain solubilized additives, including those which are added to act as a colorant, as an active water soluble ingredient, or as a fragrance.

In accordance with the second object of the present invention, a plasticized high water content cosmetic will be both sharpenable and water resistant when applied to a user's skin. This is achieved by a sodium stearate gel composition which essentially comprises, by weight, about 25–42% water; about 25–35% of a polyol or aliphatic diol vehicle such as a butylene glycol (preferably 1, 4, Butanediol); about 4–12% sodium stearate; about 0.1–2% of a carboxylated acid ester plasticizer (preferably Velsan P8-3); about 4–28% of a colorant; about 0.1–1% of a propoxylated and ethoxylated fatty alcohol as a surfactant (preferably PPG-8-CETETH-2, available as Procetyl AWS) and about 5–10% of a styrene acrylic polymer waterproofing agent (preferably Joncryl 77). The water resistant version of the cosmetic gel composition also further may include about 10% glycerin, a viscosity increasing agent (or thickener) and optionally certain solubilized additives, including those which are added to act as a colorant, as an active water soluble ingredient, or as a fragrance.

Plasticization results from the reaction of the sodium stearate with the polyol vehicle (preferably 1, 4, Butanediol) and water through the action of a carboxylated acid ester plasticizer (preferably Velsan P8-3). The reaction is assisted by a wetting action among the components when a surfactant containing a propoxylated and ethoxylated fatty alcohol (preferably Procetyl AWS) is present. Initially, a batch comprising water, 1, 4, Butanediol, a surfactant and glycerine is mixed and heated until clear, and then sodium stearate is sifted in. The plasticizer (preferably Velsan P8-3), colorants and any other water soluble ingredients then are added. The styrene acrylic polymer waterproofing agent (preferably Joncryl 77) is added last.

The novel use of sodium stearate in a range up to about 12% or less has unexpectedly and surprisingly produced a high water content cosmetic gel composition that is only a mild irritant, as classified under the Bovine Corneal Opacity and Permeability Assay assessment (developed by Gautheron, 1992) and further described below in Example 1. Also surprising is the fact that the incremental addition of both a plasticizer (Velsan P8-3) and a waterproofing agent (preferably containing styrene acrylic polymers, available as Joncryl 77) to a plasticized high water content cosmetic gel composition, where the amount of sodium stearate remains constant, does not increase the irritation score out of the mild range.

In accordance with the third object of the present invention, a sharpenable apparatus for gel cosmetic storage and application (hereafter referred to as a "gel pencil") essentially comprises a pencil barrel housing containing a plasticized high water content cosmetic gel composition as a core. The gel pencil core preferably is a water resistant sodium stearate gel composition, as noted above in connection with the first or second objects. The gel pencil barrel housing preferably is extruded or injection molded using a polypropylene-based material, and molten gel composition is directly poured into the barrel. To acheive the third object both the barrel and the core must sharpen, the core must not exude water or exhibit syneresis during storage, and the core must not crumble or break in normal use. Further, depending upon the specific core formulation chosen, the high water content cosmetic gel may define a water resistant form of cosmetic layer, after being frictionally applied to skin.

The gel pencil core diameter and barrel dimensions are not critical, and may be made of any size comfortable to the hand of a user, including those sizes commonly in use for eye liner pencils or lip liner pencils, having either wood or plastic barrels.

DETAILED DESCRIPTION OF THE INVENTION AND PREFERRED EMBODIMENTS

In accordance with a preferred embodiment of the present invention, a plasticized high water content cosmetic will be both sharpenable and water resistant when applied to a user's skin. This is achieved by a sodium stearate gel composition which ideally comprises, by weight, about 33% of water; about 29% of 1, 4, Butanediol; about 8% of sodium stearate; about 0.25% of a carboxylated acid ester plasticizer (preferably Velsan P8-3); about 16% of a colorant; about 10% glycerin; about 8% of a styrene acrylic polymer waterproofing agent (preferably Joncryl 77); and about 0.2% of a propoxylated and ethoxylated fatty alcohol as a surfactant (preferably Procetyl AWS). The colorants may be selected from common CTFA listed water-soluble colorants, such as FD&C Blue #1, Yellow #5, Red #40, or from water dispersable colorants, including colorants insoluble in a butylene glycol color grind, such as iron oxides, chromium hydroxides, ferric ferrocyanide and the like.

The plasticized high water content cosmetic gel composition further may include up to about 1% of a viscosity increasing agent (or thickener) and optionally certain solubilized additives, including any added to act as a colorant, such as an active water soluble ingredient, or a fragrance. Preferred viscosity increasing agents (or thickeners), may be selected from the group consisting of acacia, carbomer, carboxymethylhydroxycellulose, hectorite, hydroxyethylcellulose, magnesium aluminum silicate and methylcellulose. The presence of such a viscosity increasing agent surprisingly has been found to eliminate or minimize syneresis from occurring, particularly when the gel composition is contained in a pencil barrel housing and stored under elevated temperature conditions, as further described below. The plasticized high water content cosmetic gel composition preferably comprises from about 1 percent or less a viscosity increasing agent.

The preferred plasticized high water content cosmetic gel composition further may include dispersed additives such as colorants, active water soluble ingredients, and solubilized fragrances.

A gel pencil then may be prepared by directly pouring the molten, plasticized high water content cosmetic gel composition into extruded or injection molded pencil barrels.

The plasticized high water content cosmetic gel composition preferably is prepared in accordance with starting materials in the weight percentages as described above. Initially, in a tank with Lightning mixers the water, 1, 4, Butanediol, surfactant and glycerine are heated to about 80° C. and mixed until the batch is clear with a slightly yellow tinge. The sodium stearate then is sifted in and an antifoaming agent is added, if needed. While maintaining the batch at about 80° C. a carboxylated acid ester plasticizer (preferably Velsan P8-3), any pre-milled colorants and any other water soluble ingedients are added and mixed until uniformly dispersed. If a styrene acrylic polymer waterproofing agent (preferably Joncryl 77) is to be used, it is added last and mixed in until thoroughly dispersed. The barrels then are filled, while keeping the composition at about 78°–80° C.

A plasticization results from the reaction of the sodium stearate with the 1, 4, Butanediol and water through the action of a carboxylated acid ester plasticizer (preferably Velsan P8-3). The reaction is assisted by a wetting action among the components when a surfactant containing a propoxylated and ethoxylated fatty alcohol (preferably Procetyl AWS) is present.

In a preferred embodiment of a gel pencil apparatus, the barrel housing comprises polypropylene-based compositions. Polypropylene barrels are rigid, can be decorated, and can be sharpened using conventional pencil sharpeners. Preferably, the polypropylene composition incorporates various additives to improve the sharpenability of the barrel, for example, wood flour, zinc stearate, lithium stearate or calcium carbonate. Such additives are known to modify a polypropylene composition so as to allow a sharpener to trim the barrel with an even cut and without chattering, and to produce a smooth point.

In one embodiment of a waterproof type of gel pencil, the plasticized high water content cosmetic gel composition ideally essentially comprises, by weight, about 33% of water; about 29% of 1, 4, Butanediol; about 8% of sodium stearate; about 0.25% of a carboxylated acid ester plasticizer (preferably Velsan P8-3); about 16% of a colorant; about 10% glycerin; about 8% of a styrene acrylic polymer waterproofing agent (preferably Joncryl 77); and about 0.2% of a propoxylated and ethoxylated fatty alcohol as a surfactant (preferably Procetyl AWS).

In a second embodiment of a gel pencil, the plasticized high water content cosmetic gel composition further comprises up to about 1 percent or less of a viscosity increasing agent (or thickener), such as acacia, carbomer, carboxymethylhydroxycellulose, hectorite, hydroxyethylcellulose, magnesium aluminum silicate or methylcellulose. During elevated temperature storage conditions, it was noted that certain gel pencils according to the first embodiment would exhibit syneresis. The addition of a viscosity increasing agent to the gel composition was found to minimize or eliminate the tendency of a gel pencil to exude tiny drops of liquid, whether or not a waterproofing agent is employed in the gel composition.

In other embodiments of a gel pencil, the above-described embodiments of plasticized high water content cosmetic gel compositions further may comprises solubilized additives such as dispersed colorants, active water soluble ingredients, and solubilized fragrances. Various sizes for the core diameter and the barrel are possible, since the core is plasticized and will sharpen in a manner equivalent to the manner of a polypropylene. The following examples further illustrate useful applications and principles of the present invention.

EXAMPLE 1

Bovine Corneal Opacity and Permeability Assay Assessment of Three Plasticized High Water Content Cosmetic Gel Compositions A Bovine Corneal Opacity and Permeability Assay is an in vitro assessment of ocular irritation developed by Gautheron (1992). Bovine eyes are collected from an abattoir, and the corneas excised. Plastic cassettes, which mimic eye structure, are used as holders for test corneas. The posterior chamber is filled with cell support media to restore the natural shape of the cornea and to maintain cell viability. The anterior chamber is filled with the test agent, either liquid or solid, and held for 10 minutes or 4 hours, respectively. At the completion of exposure, opacity is measured by passing visible light from an opacitometer through the cornea onto the surface of a light sensor. A clear cornea that is unchanged by the test material will allow the light to pass through and be detected by the sensor.

Opaque corneas will produce light scattering (Tydall effect) and reduced detection proportional to the degree of ocular damage.

After exposure, fluorescein is added to the anterior chamber of the cassette. The amount of dye which passes through the cornea to the posterior chamber indicates the degree of corneal permeability. An increase in permeability indicates corneal damage.

The irritancy of test materials is determined by calculating an in vitro score for each treated cornea using the following formula: mean corrected opacity+(15×optical density value). The following scale is used to interpret the in vitro scores:

| In vitro score | Irritation Potential |
| --- | --- |
| 0.0 to 25.0 | mild irritant |
| 25.1 to 55.0 | moderate irritant |
| 55.1 and above | severe irritant |

Three plasticized high water content cosmetic gel composition samples were prepared and tested for ocular irritancy: AS-3-30-1, AS-3-29-3, and AW-2-51A-3. The ingredient percentages, by weight, for each sample are displayed in TABLE I. Saline was used as a negative control substance, and imidazole was used as a positive control substance.

TABLE I

|  | AS-3-30-1 | AS-3-29-3 | AW-2-51A-3 |
| --- | --- | --- | --- |
| Water | 38.78 | 33.01 | 30.00 |
| 1,4-Butanediol | 31.78 | 29.51 | 28.0 |
| Sodium Stearate | 5.00 | 5.00 | 9.50 |
| Velsan P8-3 | — | 1.00 | 2.00 |
| Black Iron Oxide | 14.07 | 14.07 | 13.64 |
| Ultramarine Blue | 1.45 | 1.45 | 1.41 |
| Ferric Ferrocyanide | 0.98 | 0.98 | 0.95 |
| Glycerin | 6.44 | 5.48 | 5.00 |
| Germaben | 1.00 | 1.00 | 1.00 |
| Joncryl 77 | — | 8.00 | 8.00 |
| Antifoam | 0.50 | 0.50 | 0.50 |
|  | 100. | 100. | 100. |

The results of the Bovine Corneal Opacity and Permeability Assay are set forth in Table II. As the percentage of sodium stearate increased, the degree of irritation increased.

TABLE II

| Material I.D. | Test Material Concen. (%) | Average Corrected Corneal Opacity vs. Negative Control | Average Corrected Optical Density | Mean In Vitro Score (Ranking) |
| --- | --- | --- | --- | --- |
| AS-3-30-1 | 20% | 8.30% | 03% | 8.73% (Mild) |
| AS-3-29-3 | 20% | 11.0% | 0.09% | 12.40% (Mild) |
| AW-2-51A-3 | 20% | 35.7 | 0.06 | 36.59% (Moderate) |
| Negative Control Saline | 0.9% | 0.0% | 0.00% | 0.00% (N/A) |
| Positive Control Imidazole | 20% | 109.4% | 0.63% | 119.02% (Severe) |

TABLE II illustrates, for both samples AS-3-30-1 and AS-3-29-3, that where a sodium stearate concentration is less than about eight percent (8%), the surprising result is that a high water content cosmetic gel composition containing sodium stearate is only at the mild irritant level. Also very surprising is the fact that even after adding 8% of Joncryl 77 as a waterproofing agent, to sample AS-3-29-3, the irritant level of that sample did not exceed the mild range. All eye products on the market have mean in vitro scores in the mild irritant range. (0–25%). For sample AW-2-51A-3, with a sodium stearate level of nine and a half percent (9.5%), and 8% of Joncryl 77, a moderate irritant level resulted. The following examples further illustrate specific cosmetic formulations which are preferred.

EXAMPLE 2

A plasticized high water content cosmetic gel composition and a gel pencil were prepared in accordance with the procedures set forth above. The resulting gel composition contained the following percentage of components:

| COMPONENT | (%, by weight) |
|---|---|
| Water | 33.95 |
| 1,4-Butanediol | 27.10 |
| Sodium Stearate | 8.00 |
| Glycerin | 5.00 |
| Joncryl 77 | 5.00 |
| Propylene Glycol | 0.56 |
| Polydimethylsiloxane | 0.50 |
| Diazolidinyl Urea | 0.30 |
| Isopropyl C12-15-Pareth-9-Carboxylate | 0.25 |
| PPG-5-Ceteth-20 | 0.20 |
| Methylparaben | 0.11 |
| Hydroxyethylcellulose | 0.10 |
| Propylparaben | 0.03 |
| Ultramarine Blue | 14.40 |
| Ultramarine Pink | 2.75 |
| Iron Oxides | 1.75 |
| | 100. |

EXAMPLE 3

A plasticized high water content cosmetic gel composition and a gel pencil were prepared in accordance with the procedures set forth above. The resulting gel composition, characterized as black in color, contained the following percentage of components:

| COMPONENT | (%, by weight) |
|---|---|
| Water | 34.05 |
| 1,4-Butanediol | 29.21 |
| Sodium Stearate | 8.00 |
| Glycerin | 5.00 |
| Joncryl 77 | 5.00 |
| Propylene Glycol | 0.56 |
| Polydimethylsiloxane | 0.50 |
| Diazolidinyl Urea | 0.30 |
| Isopropyl C12-15-Pareth-9-Carboxylate | 0.25 |
| PPG-5-Ceteth-20 | 0.20 |
| Methylparaben | 0.11 |
| Propylparaben | 0.03 |
| Iron Oxides | 15.07 |
| Ultramarine Blue | 1.72 |
| | 100. |

EXAMPLE 4

A plasticized high water content cosmetic gel composition and a gel pencil were prepared in accordance with the procedures set forth above. The resulting gel composition, characterized as grey in color, contained the following percentage of components:

| COMPONENT | (%, by weight) |
|---|---|
| Water | 34.05 |
| 1,4-Butanediol | 29.50 |
| Sodium Stearate | 8.00 |
| Glycerin | 5.00 |
| Joncryl 77 | 5.00 |
| Propylene Glycol | 0.56 |
| Polydimethylsiloxane | 0.50 |
| Diazolidinyl Urea | 0.30 |
| Isopropyl C12-15-Pareth-9-Carboxylate | 0.25 |
| PPG-5-Ceteth-20 | 0.20 |
| Methylparaben | 0.11 |
| Propylparaben | 0.03 |
| Titanium Dioxide | 10.75 |
| Iron Oxides | 5.75 |
| | 100. |

EXAMPLE 5

A plasticized high water content cosmetic gel composition and a gel pencil were prepared in accordance with the procedures set forth above. The resulting gel composition, characterized as navy blue in color, contained the following percentage of components:

| COMPONENT | (%, by weight) |
|---|---|
| Water | 34.05 |
| 1,4-Butanediol | 27.10 |
| Sodium Stearate | 8.00 |
| Glycerin | 5.00 |
| Joncryl 77 | 5.00 |
| Propylene Glycol | 0.56 |
| Polydimethylsiloxane | 0.50 |
| Diazolidinyl Urea | 0.30 |
| Isopropyl C12-15-Pareth-9-Carboxylate | 0.25 |
| PPG-5-Ceteth-20 | 0.20 |
| Methylparaben | 0.11 |
| Propylparaben | 0.03 |
| Ultramarine Blue | 14.40 |
| Ultramarine Pink | 2.75 |
| Iron Oxides | 1.75 |
| | 100. |

EXAMPLE 6

A plasticized high water content cosmetic gel composition and a gel pencil were prepared in accordance with the procedures set forth above. The resulting gel composition, characterized as brown in color, contained the following percentage of components:

| COMPONENT | (%, by weight) |
|---|---|
| Water | 34.05 |
| 1,4-Butanediol | 29.50 |
| Sodium Stearate | 8.00 |
| Glycerin | 5.00 |
| Joncryl 77 | 5.00 |
| Propylene Glycol | 0.56 |
| Polydimethylsiloxane | 0.50 |
| Diazolidinyl Urea | 0.30 |
| Isopropyl C12-15-Pareth-9-Carboxylate | 0.25 |
| PPG-5-Ceteth-20 | 0.20 |
| Methylparaben | 0.11 |
| Propylparaben | 0.03 |
| Iron Oxides | 14.30 |
| Titanium Dioxide | 2.20 |
| | 100. |

EXAMPLE 7

A plasticized high water content cosmetic gel composition and a gel pencil were prepared in accordance with the procedures set forth above. The resulting gel composition, characterized as green in color, contained the following percentage of components:

| COMPONENT | (%, by weight) |
| --- | --- |
| Water | 39.28 |
| 1,4-Butanediol | 27.50 |
| Sodium Stearate | 8.00 |
| Glycerin | 5.77 |
| Joncryl 77 | 5.00 |
| Propylene Glycol | 0.56 |
| Polydimethylsiloxane | 0.50 |
| Diazolidinyl Urea | 0.30 |
| Isopropyl C12-15-Pareth-9-Carboxylate | 0.25 |
| PPG-5-Ceteth-20 | 0.20 |
| Methylparaben | 0.11 |
| Propylparaben | 0.03 |
| Chromium Hydroxide Green | 8.23 |
| Iron Oxides | 2.70 |
| Titanium Dioxide | 1.57 |
| | 100. |

EXAMPLE 8

A plasticized high water content cosmetic gel composition and a gel pencil were prepared in accordance with the procedures set forth above. The resulting gel composition, characterized as tan in color, contained the following percentage of components:

| COMPONENT | (%, by weight) |
| --- | --- |
| Water | 34.05 |
| 1,4-Butanediol | 29.50 |
| Sodium Stearate | 8.00 |
| Glycerin | 5.00 |
| Joncryl 77 | 5.00 |
| Propylene Glycol | 0.56 |
| Polydimethylsiloxane | 0.50 |
| Diazolidinyl Urea | 0.30 |
| Isopropyl C12-15-Pareth-9-Carboxylate | 0.25 |
| PPG-5-Ceteth-20 | 0.20 |
| Methylparaben | 0.11 |
| Propylparaben | 0.03 |
| Iron Oxides | 10.00 |
| Titanium Dioxide | 6.50 |
| | 100. |

While the present invention has been described with respect to what is presently considered to be the preferred embodiments, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

We claim:

1. A plasticized high water content cosmetic gel composition consisting essentially of:

from about 25 percent to about 50 percent water;

from about 25 percent to about 35 percent of an aliphatic diol vehicle;

from about 4 percent to about 12 percent sodium stearate;

from about 4 percent to about 28 percent of colorants;

from about 0.1 percent to about 2 percent of a carboxylated acid ester plasticizer; and from about 0.1 percent to about 1 percent of a surfactant.

2. A plasticized high water content cosmetic gel composition according to claim 1, wherein said aliphatic diol vehicle comprises 1,4-Butanediol and further comprising from about about 1 percent or less of a viscosity increasing agent.

3. A plasticized high water content cosmetic gel composition according to claim 2, wherein the viscosity increasing agent is selected from the group consisting of acacia, carbomer, carboxymethylhydroxycellulose, hectorite, hydroxyethylcellulose, magnesium aluminum silicate or methylcellulose.

4. A plasticized high water content cosmetic gel composition according to claim 1, further comprising from about 5 percent to about 10 percent of glycerine.

5. A plasticized high water content cosmetic gel composition according to claim 1, further comprising solubilized additives selected from the group consisting of colorants, active water soluble ingredients and fragrances.

6. A plasticized high water content cosmetic gel composition according to claim 1, wherein said surfactant further comprises a propoxylated and ethoxylated fatty alcohol.

7. A plasticized high water content cosmetic gel composition having water resistant characteristics when applied to the skin, consisting essentially of:

from about 25 percent to about 50 percent water;

from about 25 percent to about 35 percent of an aliphatic diol vehicle;

from about 4 percent to about 12 percent sodium stearate;

from about 4 percent to about 28 percent of colorants;

from about 0.1 percent to about 2 percent of a carboxylated acid ester plasticizer;

from about 0.1 percent to about 1 percent of a surfactant; and from about 5 percent to about 10 percent of a waterproofing agent comprising styrene acrylic polmers.

8. A plasticized high water content cosmetic gel composition according to claim 7, wherein said aliphatic diol vehicle comprises 1,4-Butanediol and further comprising from about about 1 percent or less of a viscosity increasing agent.

9. A plasticized high water content cosmetic gel composition according to claim 7, wherein the viscosity increasing agent is selected from the group consisting of acacia, carbomer, carboxymethylhydroxycellulose, hectorite, hydroxyethylcellulose, magnesium aluminum silicate or methylcellulose.

10. A plasticized high water content cosmetic gel composition according to claim 7, further comprising from about 5 percent to about 10 percent of glycerine.

11. A plasticized high water content cosmetic gel composition according to claim 7, further comprising solubilized additives selected from the group consisting of colorants, active water soluble ingredients or fragrances.

12. A plasticized high water content cosmetic gel composition according to claim 7, wherein said surfactant further comprises a propoxylated and ethoxylated fatty alcohol.

13. An apparatus for cosmetic storage and application, comprising:

a pencil barrel housing; and a plasticized high water content cosmetic gel composition contained as a core within said housing, said gel composition comprising:

from about 25 percent to about 50 percent water;

from about 25 percent to about 35 percent of an aliphatic diol vehicle;

from about 4 percent to about 12 percent sodium stearate;

from about 4 percent to about 28 percent of colorants;

from about 0.1 percent to about 2 percent of a carboxylated acid ester plasticizer; and from about 0.1 percent to about 1 percent of a surfactant.

14. A plasticized high water content cosmetic gel composition according to claim 13, wherein said aliphatic diol vehicle comprises 1,4-Butanediol and further comprising from about about 1 percent or less of a viscosity increasing agent.

15. A plasticized high water content cosmetic gel composition according to claim 14, wherein the viscosity increasing agent is selected from the group consisting of acacia, carbomer, carboxymethylhydroxycellulose, hectorite, hydroxyethylcellulose, magnesium aluminum silicate or methylcellulose.

16. A plasticized high water content cosmetic gel composition according to claim 13, further comprising from about 5 percent to about 10 percent of glycerine.

17. A plasticized high water content cosmetic gel composition according to claim 13, further comprising solubilized additives selected from the group consisting of colorants, active water soluble ingredients and fragrances.

18. A plasticized high water content cosmetic gel composition according to claim 13, wherein said surfactant further comprises a propoxylated and ethoxylated fatty alcohol.

19. An apparatus for cosmetic storage and application according to claim 13, wherein the pencil barrel housing comprises a plastic composition.

20. An apparatus for cosmetic storage and application according to claim 19, wherein the plastic barrel housing comprises an injection molded or extruded polypropylene composition, and one or more additive to improve the sharpenability of the barrel that is selected from the group consisting of wood flour, zinc stearate, lithium stearate and calcium carbonate.

21. An apparatus for cosmetic storage and application, comprising:

a pencil barrel housing; and a plasticized high water content cosmetic gel composition having water resistant characteristics when applied to the skin, consisting essentially of:

from about 25 percent to about 50 percent water;

from about 25 percent to about 35 percent of an aliphatic diol vehicle;

from about 4 percent to about 12 percent sodium stearate;

from about 4 percent to about 28 percent of colorants;

from about 0.1 percent to about 2 percent of a carboxylated acid ester plasticizer;

from about 0.1 percent to about 1 percent of a surfactant; and from about 5 percent to about 10 percent of a waterproofing agent comprising styrene acrylic polmers.

22. A plasticized high water content cosmetic gel composition according to claim 21, wherein said aliphatic diol vehicle comprises 1,4-Butanediol and further comprising from about about 1 percent or less of a viscosity increasing agent.

23. A plasticized high water content cosmetic gel composition according to claim 22, wherein the viscosity increasing agent is selected from the group consisting of acacia, carbomer, carboxymethylhydroxycellulose, hectorite, hydroxyethylcellulose, magnesium aluminum silicate or methylcellulose.

24. A plasticized high water content cosmetic gel composition according to claim 21, further comprising from about 5 percent to about 10 percent of glycerine.

25. A plasticized high water content cosmetic gel composition according to claim 21, further comprising solubilized additives selected from the group consisting of colorants, active water soluble ingredients and fragrances.

26. A plasticized high water content cosmetic gel composition according to claim 21, wherein said surfactant further comprises a propoxylated and ethoxylated fatty alcohol.

27. An apparatus for cosmetic storage and application according to claim 21, wherein the pencil barrel housing comprises a plastic composition.

28. An apparatus for cosmetic storage and application according to claim 27, wherein the plastic barrel housing comprises an injection molded or extruded polypropylene composition, and one or more additive to improve the sharpenability of the barrel that is selected from the group consisting of wood flour, zinc stearate, lithium stearate and calcium carbonate.

* * * * *

UNITED STATES PATENT AND TRADEMARK OFFICE
CERTIFICATE OF CORRECTION

PATENT NO. : 5,753,243
DATED : May 19, 1998
INVENTOR(S) : Cunningham et al.

It is certified that error appears in the above-identified patent and that said Letters Patent is hereby corrected as shown below:

Title page,
In the title, substitute -- THEREFOR -- for "THERERFORE".

Claim 9,
Line 2, delete "7" and substitute -- 8 -- therefor.

Claim 14,
Lines 1 and 2, delete "A plasticized high water content cosmetic gel composition" and substitute -- An apparatus -- therefor.

Claim 15,
Lines 1 and 2, delete "A plasticized high water content cosmetic gel composition" and substitute -- An apparatus -- therefor.

Claim 16,
Lines 1 and 2, delete "A plasticized high water content cosmetic gel composition according to claim 13, further comprising" and substitute -- An apparatus according to claim 13, wherein said plasticized high water content cosmetic gel composition further comprises -- therefor.

Claim 17,
Lines 1 and 2, delete "A plasticized high water content cosmetic gel composition according to claim 13, further comprising" and substitute -- An apparatus according to claim 13, wherein said plasticized high water content cosmetic gel composition further comprises -- therefor.

Claim 18,
Lines 1 and 2, delete "A plasticized high water content cosmetic gel composition" and substitute -- An apparatus -- therefor.

Claim 22,
Lines 1 and 2, delete "A plasticized high water content cosmetic gel composition" and substitute -- An apparatus -- therefor.

Claim 23,
Lines 1 and 2, delete "A plasticized high water content cosmetic gel composition" and substitute -- An apparatus -- therefor.

UNITED STATES PATENT AND TRADEMARK OFFICE
CERTIFICATE OF CORRECTION

PATENT NO. : 5,753,243
DATED : May 19, 1998
INVENTOR(S) : Cunningham et al.

It is certified that error appears in the above-identified patent and that said Letters Patent is hereby corrected as shown below:

Claim 24,
Lines 1 and 2, delete "A plasticized high water content cosmetic gel composition according to claim 21, further comprising" and substitute -- An apparatus according to claim 21, wherein said plasticized high water content cosmetic gel composition further comprises -- therefor.

Claim 25,
Lines 1 and 2, delete "A plasticized high water content cosmetic gel composition according to claim 21, further comprising" and substitute -- An apparatus according to claim 21, wherein said plasticized high water content cosmetic gel composition further comprises -- therefor.

Claim 26,
Lines 1 and 2, delete "A plasticized high water content cosmetic gel composition" and substitute -- An apparatus -- therefor.

Signed and Sealed this

Twenty-fifth Day of December, 2001

Attest:

*Attesting Officer*

JAMES E. ROGAN
*Director of the United States Patent and Trademark Office*